United States Patent [19]

Brake

[11] Patent Number: 5,264,617
[45] Date of Patent: Nov. 23, 1993

[54] PREPARATION OF ALKYL ESTERS BY DEPOLYMERIZATION

[75] Inventor: Loren D. Brake, Wilmington, Del.

[73] Assignee: E. I. Du Pont de Nemours and Company, Wilmington, Del.

[21] Appl. No.: 797,502

[22] Filed: Nov. 22, 1991

[51] Int. Cl.$^5$ .................. C07C 69/66; C07C 51/42; C07C 59/08
[52] U.S. Cl. .................. 560/179; 562/580; 562/589; 549/274; 528/300
[58] Field of Search .................. 560/179; 549/274; 562/589, 580

[56] References Cited

U.S. PATENT DOCUMENTS

| 2,231,953 | 2/1941 | Ruxicka | 92/17 |
| 3,284,417 | 11/1966 | Hostettler et al. | 260/78.3 |
| 3,578,700 | 5/1971 | Klootwijk et al. | 260/484 |
| 4,727,163 | 2/1988 | Bellis | 549/274 |
| 4,797,468 | 1/1989 | De Vries | 528/354 |
| 4,835,293 | 5/1989 | Bhatia | 549/274 |

FOREIGN PATENT DOCUMENTS

90/01521 2/1990 PCT Int'l Appl.

Primary Examiner—José G. Dees
Assistant Examiner—Porfirio Nazario

[57] ABSTRACT

Depolymerizing polyhydroxy acid by heating with the alcohol of 1-6 carbon atoms in the presence of an acid catalyst to produce an alkyl ester.

30 Claims, No Drawings

PREPARATION OF ALKYL ESTERS BY DEPOLYMERIZATION

BACKGROUND OF THE INVENTION

1. Field of the Invention

The present invention relates to the preparation of alkyl esters by the depolymerization of high molecular weight polyhydroxy acid (PHA) with an alcohol of 1–6 carbon atoms in the presence of an acid catalyst. More specifically, the present invention relates to the recovery of hydroxy acid value from a polyhydroxy acid polymer-containing source such as food container trash.

2. Description of the Related Art

Shaped articles of high molecular weight (at least 10,000, and normally 15,000 to 500,000 MW) polyhydroxy acids (PHA), particularly polylactic acid (PLA, polylactide), polyglycolic acid (PGA, polyglycolide), and copolymers thereof, have been known for years. An important property of these polymers is that they are slowly hydrolyzable and thereafter biodegradable to environmentally benign by-products. Consequently high molecular weight PHA polymer shaped articles are finding increasing application as replacements for polystyrene and other non-degradable polymers in products that will degrade in a landfill, such as fast food containers (Sinclair et al., WO90/01521, Feb. 22, 1990).

While this is a significant step in minimizing litter and long-term landfill disposal, discarding high molecular weight polyhydroxy acid articles for natural destruction by hydrolysis has the cost penalty of discarding the valuable polyhydroxy acid.

Although the hydrolysis of PHAs is well known, heretofore it has not been achievable in a time frame to permit recovery and reuse of the valuable hydroxy acid (HA) moities. In fact, although degradable, the time for degradation of high molecular weight PHAs is so long as not to offer a lessening burden on landfills.

Thus, there is a need for an economical method to recover and recycle the polyhydroxy acid content of this source of waste material and avoid burdening landfills with this waste.

The most economical routes for PHA production start with the acid such as tactic acid. The acid is converted to an ester, dimerized to a cyclic ring such as lactide, which is then polymerized to PHA. This is a complicated and costly process. See Bhatia U.S. Pat. No. 4,835,293 (May 30, 1989); Bellis U.S. Pat. No. 4,727,163 (Feb. 23, 1988); Klootwijk U.S. Pat. No. 3,578,700; Hostettler et. al. U.S. Pat. No. 3,284,417; and De Vries U.S. Pat. No. 4,797,468 (Jan. 10, 1989).

Bhatia U.S. Pat. No. 5,136,057 discloses the depolymerization of low molecular weight oligomers remaining after PHA polymerization. This patent application does not address the problem of recovery of the monomeric values from used high molecular weight PHA articles.

Copending and commonly assigned U.S. patent application Ser. Nos. 07/797,503, 07/796,273, 07/796,272 and 07/796,274 disclose the recovery of PHA's, respectively, in the presence of water and acid; in water under heat and pressure; in the presence of specific amines; and in the presence of water and lower alkyl alcohol.

The aforementioned patents and patent applications are incorporated herein by reference.

SUMMARY OF THE INVENTION

The present invention provide a method of preparing an ester from a high molecular weight polyhydroxy acid polymer comprising mixing said polymer with an alkyl alcohol containing 1–6 carbon atoms in the presence of a catalytically sufficient amount of an acid while maintaining the polymer/catalyst mixture at sufficient temperature and pressure for a sufficient time to depolymerize the polymer. In one embodiment of the invention the polymer is selected from group consisting of polylactide, polyglycolide, and polymers containing a major proportion of polylactide and polyglycolide polymerized with up to 30% of another monomer selected from the group consisting of epsilon-caprolactone, delta-valerolactone, 1,5-dioxepen-2-one, 1,4-dioxan-2-one, beta-butyrolactone, beta-propiolactone, 6-methyl-2,5-morpholinedione and mixtures thereof. Typically the temperature of the process is in the range of 120° to 200° C. and the time for conversion is in the range of ¼ to 16 hours to reach depolymerization equilibrium.

The present invention also provides a process of preparing an ester from a high molecular weight polyhydroxy acid from trash, comprising the setps of:

(a) mixing waste with a $C_1$ to $C_6$ alkyl alcohol present in an amount of at least 1 mole of alcohol per hydroxy acid equivalent;

(b) heating the mixture to solubilize the polyhydroxy acid;

(c) removing the undissolved trash material; and (d) adding a catalytically sufficient amount of an acid while maintaining the resulting polymer/catalyst/alcohol mixture at sufficient temperature and pressure for a sufficient time to depolymerize said polymer and form said ester.

The present invention further provides a process for recoverying hydroxy acid value from a polyhydroxy acid polymer-containing source comprising the steps of:

(a) contacting a polyhydroxy acid polymer-containing material, wherein said polyhydroxy acid polymer-containing material is contaminated with or constitutes trash, with an alcohol containing 1–6 carbon atoms in the presence of a catalytically sufficient amount of an acid while maintaining the polymer/catalyst mixture at sufficient temperature and pressure for a sufficient time to depolymerize said polymer and form an ester; and (b) thereafter isolating and recovering said ester.

DESCRIPTION OF THE PREFERRED EMBODIMENTS

The present invention relates to an inexpensive depolymerization of PHA in the preparation of a $C_1$ to $C_6$ alkyl ester. In the process of the present invention PHA is mixed with an alkyl alcohol of 1 to 6 carbon atoms and an acid catalyst. Adequate heat and pressure are applied, to raise the temperature to that needed to depolymerize the particular PHA. When depolymerization is completed to the desired extent, the ester product and excess alcohol can be recovered by distillation, under vacuum if needed. Before distillation it may be desirable to neutralize the acid catalyst to minimize conversion of the ester to low molecular weight polymer. The ester can then be recycled directly into the PHA production process.

The process is particularly useful in the recovery and conversion to esters of high molecular weight polylactic and polyglycolic acids, and copolymers thereby, of molecular weights above 10,000 and normally 15,000–500,000 MW.

When adequate alcohol is used, normally at least a slight excess of the molar ester requirements and preferrably a stoichiometric excess of the order of 2:1, depolymerization conversion to ester in excess of 60%, and normally in the range of 70–90%, of theoretical is achieved, leaving a heel rich in PHA equivalents. If desired this heel, with or without the addition of new PHA, can be sequentially reprocessed one or more times with further additions of alcohol. If the heel is to be preprocessed, normally the acid catalyst is not neutralized, in which case additional catalyst is not needed. Even if additional PHA is added to the heel, it normally is not necessary to add further acid catalyst. By this series of treatments, substantially 100% conversion of PHA to the ester can be achieved.

This process is used for the depolymerization of the common PHAs, and co- and ter-polymers therewith. It is effective with a wide range of molecular weight polymers, the preferred range being from 50,000 to 500,000 or higher. It is most useful in the depolymerization of polylactide, polyglycolide and copolymers thereof; also it is useful for PHAs containing these polymer moities polymerized with other monomers. These co- and ter-polymers preferably contain at least 70% of PLA and/or PGA moities, and not more than 30% of the other monomer. Examples of other suitable monomer units are:
epsilon-caprolactone,
delta-valerolactone,
1,5-dioxepan-2-one,
1,4-dioxan-2-one,
beta-butyrolactone, and
beta-propiolactone, and
6-methyl-2,5-morpholinedione.
The particular other monomer units present in the PHA to be depolymerized are not critical, the present process having wide applicability in depolymerizing and recovering the monomer value of PHAs.

The amount of alcohol used affects the time required to carry out the depolymerization and the percent conversion. Normally a molar ratio of alcohol to PHA (on an acid unit basis) in the range of 1:1 to 2:1 is used. Since an excess of alcohol favors depolymerization, preferably a substantial excess is used, but not so much as to make alcohol recovery an excessive expense.

Increased alcohol content and temperature speed the depolymerization and ester formation. In many cases overall economies and reaction kinetics dictate depolymerizing and esterification at atmospheric pressure although elevated pressure sometimes is needed to reach the necessary temperature for depolymerization. However, it may be desirable to use elevated pressures, up to about 500 psi, when depolymerization of the particular PHA and ester formation requires such pressure, or when high depolymerization rate at elevated temperatures is desired. This is particularly true with the lower $C_1$ to $C_3$ alcohols that have atmospheric boiling temperatures below 110° C.

Elevated temperatures, below decomposition, also favor the reaction. Temperatures normally in the range of 100°–250° C. or higher, preferably 120°–200° C. are employed. The particular temperature selected is dependent not only on the desired reaction speed, but also on the pressure to be used, the reaction time and the physical and chemical nature of the acid catalyst.

Various acid catalysts are effective in the present process. In general strong organic or inorganic acids that do not react with the PHA to form depolymerization products or form undesirable by-products can be used. Liquid or water soluble solid catalysts are preferred for ease of use and concentration. Sulfuric acid (6–36N) and and p-toluene sulfonic acid (solid) are excellent inexpensive acid catalysts. Methane sulfonic acid is also acceptable. Hydrochloric acid, although an effective catalyst, is generally undesirable because of its excessive corrosiveness to equipment. Very small quantities of catalyst are required, normally in the weight range of 0.01 to 2% of acid molecule or more, preferably 0.1% to 0.5% of PHA to be catalytically effective. The depolymerization proceeds even if large quantities of water are introduced with the acid (dilute acid). However, this is undesirable because the large amounts of water will unduly limit the ester formation.

A very important economical aspect of the present process is the speed of the depolymerization. By selecting optimal reaction conditions, reactants and catalyst, batch depolymerizations of significant quantities of PHA can be depolymerized often in 1 hour and even in as little as 15 minutes. Reactor design, i.e., agitation, etc., also plays an important role in reaction rate. Where speed is less a factor than other economies, batch times as long as 16 hours may be appropriate.

Continuous process depolymerization is also possible, such as with the feed materials being continuously introduced into the first depolymerization stage of a multistage system, and the ester product and excess alcohol being recovered from the last stage. Ester and alcohol can also be taken out of the system at intermediate points.

As aforementioned after depolymerization, neutralization of the acid catalyst may be desired, unless of course there is to be subsequent depolymerization steps of the heel. Any non-reactive, non-volatile base or basic salt can effectuate neutralization. Typical inexpensive neutralizing agents are sodium and potassium carbonates and hydroxides and ammonia.

The alkyl ester is recoverable from the reaction medium by selective distillation to recover separately the excess alcohol and the ester. Alternatively, the alcohol/ester mixture may be introduced into the polyhydroxy acid manufacture process.

The following examples illustrate the preferred practice of the present invention.

EXAMPLE 1

A mixture of 100 grams polylactide (200,000 M.W.), 200 grams n-butanol and 0.2 gram p-toluenesulfonic acid is heated at 120° C. for twelve hours in a 500 cc round bottom flask fitted with a reflux condenser. After cooling to room temperature. 0.3 grams sodium carbonate is added to neutralize the acid and the resulting mixture is distilled under vacuum to recover the unconverted butanol at b.p. 66° C. at 80 mm and butyl lactate at b.p. 106° C. at 55 mm. The unconverted polylactide remains as the distillation heel. The recovered butyl lactate represented a 83% polylactide conversion.

EXAMPLE 2

A mixture of 100 grams polylacide (200,000 M.W.), 200 grams n-butanol and 0.5 gram 36N sulfuric acid is heated at 120° C. for twelve hours. The reaction product is distilled under vacuum as described in Example 1 without neutralizing the sulfuric acid to recover the unconverted butanol and butyl lactate. The polylactide conversion was 81% to butyl lactate.

EXAMPLE 3

A mixture of 100 grams polylactide (200,000 M.W.), 200 grams n-butanol and 1.0 gram 36N sulfuric acid is heated at 120° C. for five hours in a 500 cc round bottom flask fitted with a reflux condenser. The reaction product is distilled under vacuum as described in Example 1 without neutralizing the sulfuric acid to recover the unconverted butanol and butyl lactate. The polylactide conversion was 75% to butyl lactate.

EXAMPLE 4

A mixture of 75 grams polylactide (200,000 M.W.), 150 grams n-butanol and 0.1 gram p-toluenesulfonic acid is heated at 120° C. for three hours in a 500 cc round bottom flask fitted with a reflux condenser. The reaction product is distilled under vacuum as described in Example 1 to recover the unconverted butanol and butyl lactate. The distillation heel weighed 60 grams.

The 60 gram heel is mixed with 90 grams n-butanol and heated at 120° C. for three hours as described above. The reaction product is distilled under vacuum to recover the unconverted butanol and butyl lactate. The distillation heel weighed 14 grams.

The 14 gram heel is mixed with 27 grams n-butanol and heated at 130° C. for three hours as described above. The reaction product is distilled under vacuum as described in Example 1 to recover the unconverted butanol and butyl lactate. The distillation heel weighed 3 grams.

The combined three stage reaction demonstrated the recycle of the distillation heel to the depolymerization reaction step without additional acid catalyst being added to achieve an overall 97% conversion of polylactide to butyl lactate.

Examples 5 thru 8 compare the depolymerization of polylactide vs temperature at a constant reaction time to measure the temperature required to achieve the maximum polylactide conversion with this set of feed compositions and reaction conditions.

EXAMPLE 5

A mixture of 75 grams polylactide (200,000 M.W.), 150 grams n-butanol and 0.5 gram 36N sulfuric acid is heated at 120° C. for two hours in a 500 cc round bottom flask fitted with reflux condenser at atmospheric pressure. The reaction product was cooled to room temperature and 0.7 gram sodium carbonate is added to the reaction product to neutralize the acid catalyst. The resulting mixture is distilled under vacuum as described in Example 1 to recover the butyl lactate and unreacted butanol. The polylactide conversion was 36% to butyl lactate.

EXAMPLE 6

A mixture of 75 grams polylactide (200,000 M.W.), 150 grams n-butanol and 0.5 gram 36N sulfuric acid is heated at 150° C. for two hours under autogenous pressure in a 400 cc agitated pressure vessel. To the product is added 0.7 gram sodium carbonate to neutralize the acid catalyst. The resulting mixture is distilled under vacuum as described in Example 1 to recover the butyl lactate and unreacted butanol. The polylactide conversion was 69% to butyl lactate.

EXAMPLE 7

A mixture of 75 grams polylactide (200,000 MW), 150 grams n-butanol and 0.5 gram 36N sulfuric acid is heated at 170° C. for two hours under autogenous pressure in a 400 cc agitated pressure vessel. To the product is added 0.7 gram sodium carbonate to neutralize the acid catalyst. The resulting mixture is distilled under vacuum as described in Example 1 to recover the butyl lactate and unreacted butanol. The polylactide conversion was 84% to butyl lactate.

EXAMPLE 8

A mixture of 75 grams polylactide (200,000 M.W), 150 grams n-butanol and 0.5 gram sulfuric acid is heated at 190° C. for two hours under autogenous pressure in a 400 cc agitated pressure vessel. To the product is added 0.7 gram sodium carbonate to neutralize the acid catalyst. The resulting mixture is distilled under vacuum as described in Example 1 to recover the butyl lactate and unreacted butanol. The polylactide conversion was 83% to butyl lactate.

EXAMPLE 9

A mixture of 75 grams polylactide (200,000 MW), 96 grams methanol and 0.5 gram sulfuric acid is heated at 150° C. for two hours under autogenous pressure in a 400 cc agitated pressure vessel. The reaction product is distilled recover the unconverted methanol at b.p. 65° C. and methyl lactate at b.p. 144° C. The polylactide conversion was 87% to methyl lactate.

EXAMPLE 10

A mixture of 75 grams polylactide (200,000 M.W.), 92 grams ethanol and 0.5 gram sulfuric acid is heated at 150° C. for two hours under autogenous pressure in a 400 cc agitated pressure vessel. The reaction product is distilled to recover the unconverted ethanol at b.p. 79° C. and ethyl lactate at b.p. 154° C. The polylactide conversion was 78% to ethyl lactate.

EXAMPLE 11

The following example demonstrates the recovery of simulated throwaway polylactide waste articles mixed with paper and food from a fast food establishment.

A mixture of 100 grams polylactide (300,000 M.W.), 200 grams n-butanol, 0.5 grams brown bag, 2.0 grams bread, 5.0 grams sausage and 0.3 grams wax paper is heated at 120° C. for two hours in a 500 cc round bottom flask fitted with a reflux condenser. The resulting mixture is filtered hot through a steam heated buchner funnel to separate the insoluble material. The solids are washed with 50 grams hot n-butanol. 0.7 grams p-toluenesulfonic acid is added to the filtrate in a 500 cc round bottom flask fitted with a reflux condenser and heated at 120° C. for 11 hours. The reaction product is distilled under vacuum as described in Example 1 to recover the butyl lactate and unconverted butanol. The polylactide conversion was 55% to butyl lactate.

EXAMPLE 12

A mixture of 75 grams polylactide (200,000 M.W), 150 grams n-butanol, 20 grams water and 0.5 gram 36N sulfuric acid is heated at 150° C. for two hours under autogenous pressure in a 400 cc agitated pressure vessel. The reaction product is distilled at atmospheric pressure to remove the water and continued under vacuum as described in Example 1 to recover the unconverted butanol and butyl lactate. The polylactide conversion was 58% to butyl lactate.

EXAMPLES 13-15

Following the procedure of Example 8 using molar equivalent amounts of polyhydroxyacid and alcohol as those used in Example 8, other polyhydroxyacids and polyhydroxyacid copolymers are depolymerized. The following Table shows a list of polyhydroxyacids that are depolymerized to give the listed products:

TABLE

| | Polyhydroxyacid | Products |
|---|---|---|
| 13. | Polyglycolide | butyl glycolate |
| 14. | 50-50 co-polymer of lactic acid and glycolic acid | butyl lactate & butyl glycolate |
| 15. | 70-30 co-polymer of lactic acid and epsilon-caprolactone | butyl lactate & butyl 5-hydroxy caprolactate |

EXAMPLE 16

A mixture of 75 grams polylactide (200,000 M.W.) 150 grams n-butanol and 1.0 grams 18 N sulfuric acid is heated at 170° C. for two hours under autogenous pressure in a 400 cc agitated pressure vessel. To the product is added 0.7 gram sodium carbonate to neutralize the acid catalyst. The resulting mixture is distilled under vacuum as described in Example 1 to recover the butyl lactate and unreacted butanol. The polylactide conversion was 80% to butyl lactate.

EXAMPLE 17

A mixture of 75 grams polylactide (200,000 M.W.), 150 grams n-butanol and 4.0 grams 4.5 N sulfuric acid is heated at 70° C. for two hours under autogenous pressure in a 400 cc agitated pressure vessel. To the product is added 0.7 gram sodium carbonate to neutralize the acid catalyst. The resulting mixture is distilled under vacuum as described in Example 1 to recover the butyl lactate and unreacted butanol. The polylactide conversion was 82% to butyl lactate.

What is claimed:

1. The process of preparing an ester from a high molecular weight polyhydroxy acid polymer comprising mixing said polymer with an alkyl alcohol containing 1-6 carbon atoms in the presence of a catalytically sufficient amount of an acid while maintaining the polymer/catalyst mixture at a temperature of 100°-250° C. for a sufficient time to depolymerize the polymer.

2. The process of claim 1 wherein the polymer contains at least a major proportion of polylactide.

3. The process of claim 1 wherein said polymer is selected from the group consisting of polylactide, polyglycolide, and polymers containing a major proportion of polylactide and polyglycolide polymerized with up to 30% of another monomer selected from the group consisting of epsilon-caprolactone, delta-valerolactone, 1,5-dioxepen-2-one, 1,4-dioxan-2-one, beta-butyrolactone, beta-propiolactone, 6-methyl-2,5-morpholinedione and mixtures thereof.

4. The process of claim 2 wherein said temperature is in the range of 120°-200° C.

5. The process of claim 2 wherein the time is in the range of ¼-16 hours.

6. The process of claim 1 wherein the product is the alcohol ester.

7. The process of claim 1 wherein the alcohol to polyhydroxy acid molar ratio is in the range of 1:1 to 2:1.

8. The process of claim 6 wherein the alcohol is n-butanol.

9. The process of claim 6 wherein the alcohol is methanol.

10. The process of claim 6 wherein the alcohol is ethanol.

11. The process of claim 1 wherein the acid is selected from the group consisting of sulfuric acid, p-toluenesulfonic acid, and methane sulfonic acid.

12. The process of claim 1 wherein the remaining heel is reprocessed by further heating after adding more of said alcohol to the heel.

13. The process of claim 1 wherein polymer is continuously added and ester product and alcohol are continuously removed.

14. The process of claim 1 wherein said catalyst is a strong acid that does not react with the products of the depolymerization.

15. The process of preparing an ester from a high molecular weight polyhydroxy acid from trash, comprising the steps of:
(a) mixing polyhydroxy acid containing trash with a $C_1$ to $C_6$ alkyl alcohol, said alcohol being present in an amount of at least 1 mole of alcohol per mole of hydroxy acid equivalent in said trash;
(b) heating the mixture to solubilize the polyhydroxy acid;
(c) removing the undissolved trash material;
(d) adding a catalytically sufficient amount of an acid while maintaining the resulting polyhydroxy acid/catalyst/alcohol mixture at a temperature of 100°-250° C. for a sufficient time to depolymerize said polyhydroxy acid and form said ester.

16. The process of claim 15 wherein the polymer contains at least a major proportion of polylactide.

17. The process of claim 15 wherein said polymer is selected from the group consisting of polylactide, polyglycolide, and polymers containing a major proportion of polylactide and polyglycolide polymerized with up to 30% of another monomer selected from the group consisting of epsilon-caprolactone, delta-valerolactone, 1,5-dioxepen-2-one, 1,4-dioxan-2-one, beta-butyrolactone, beta-propiolactone, 6-methyl-2,5-morpholinedione and mixtures thereof.

18. The process of claim 16 wherein said temperature is in the range of 120°-200° C.

19. The process of claim 16 wherein the time to solubilize is in the range of ¼-16 hours and the time sufficient to reach molar equilibrium depolymerization is in the range of ¼-16 hours.

20. The process of claim 15 wherein the product of depolymerization is the alcohol ester.

21. The process of claim 15 wherein the alcohol to polyhydroxy acid molar ratio is in the range of 1:1 to 2:1.

22. The process of claim 20 wherein the alcohol is n-butanol.

23. The process of claim 20 wherein the alcohol is methanol.

24. The process of claim 20 wherein the alcohol is ethanol.

25. The process of claim 15 wherein the acid is selected from the group consisting of sulfuric acid, p-toluenesulfonic acid, and methane sulfonic acid.

26. The process of claim 15 wherein the remaining heel is reprocessed by further heating after adding more of said alcohol to the heel.

27. The process of claim 15 wherein said trash is continuously added and said ester and said alcohol are continuously removed.

28. The process of claim 15 wherein said catalyst is a strong acid that does not react with the products of the depolymerization.

29. A process for forming and recovering the ester of a hydroxy acid from a polyhydroxy acid polymer-containing source comprising the steps of:

(a) contacting a polyhydroxy acid polymer-containing material, wherein said polymer-containing material is contaminated with or constitutes trash, with an alcohol containing 1-6 carbon atoms in the presence of a catalytically sufficient amount of an acid while maintaining the polymer/catalyst mixture at a temperature of 100°-250° C. for a sufficient time to depolymerize said polymer and form an ester; and (b) thereafter isolating and recovering said ester.

30. The process of claim 29 wherein the alcohol is n-butanol.

* * * * *